United States Patent [19]

Degnan, Jr. et al.

[11] Patent Number: 5,026,921

[45] Date of Patent: Jun. 25, 1991

[54] AROMATIZATION PROCESS UTILIZING A PILLARED LAYERED SILICATE PLUS GALLIUM OR ZINC

[75] Inventors: Thomas F. Degnan, Jr., Morristown; Ivy D. Johnson, Medford, both of N.J.

[73] Assignee: Mobil Oil Corporation, Fairfax, Va.

[21] Appl. No.: 454,531

[22] Filed: Dec. 21, 1989

[51] Int. Cl.$^5$ .................... C07C 2/00; C07C 5/367
[52] U.S. Cl. ................... 585/415; 585/418; 585/419; 585/420
[58] Field of Search ............ 585/418, 419, 420, 415

[56] References Cited

U.S. PATENT DOCUMENTS

| | | | |
|---|---|---|---|
| 3,756,942 | 9/1973 | Cattanach | 206/137 |
| 4,180,689 | 12/1979 | Davies et al. | 585/407 |
| 4,216,188 | 8/1980 | Shabria et al. | 502/63 |
| 4,248,739 | 2/1981 | Vaughan et al. | 502/84 |
| 4,490,569 | 12/1984 | Chu et al. | 502/343 |
| 4,490,569 | 12/1984 | Chu et al. | 585/415 |
| 4,515,901 | 5/1985 | Elattar | 502/84 |
| 4,637,991 | 1/1987 | Battiste et al. | 502/68 |
| 4,754,091 | 6/1988 | Jezl et al. | 585/418 |
| 4,806,699 | 2/1989 | Smith et al. | 585/417 |
| 4,814,539 | 3/1989 | Jezl | 585/415 |
| 4,822,942 | 4/1989 | Dessau et al. | 585/435 |
| 4,859,648 | 8/1989 | Landis et al. | 502/242 |

Primary Examiner—Patrick P. Garvin
Assistant Examiner—George R. Fowson
Attorney, Agent, or Firm—Alexander J. McKillop; Charles J. Speciale; Edward F. Kenehan, Jr.

[57] ABSTRACT

Therein is provided a process for the aromatization of non-aromatic hydrocarbons having at least two carbon atoms. The non-aromatic feed is contacted with a catalyst which includes gallium or zinc which is incorporated into or onto a pillared layered silicate. A preferred pillared layered silicate is kenyaite containing interspathic silica.

9 Claims, No Drawings

AROMATIZATION PROCESS UTILIZING A PILLARED LAYERED SILICATE PLUS GALLIUM OR ZINC

BACKGROUND

The present invention relates to aromatization of non-aromatic $C_2$ to $C_{12}$ hydrocarbons using a catalyst which comprises a layered silicate and gallium or zinc.

The production of aromatic hydrocarbons from non-aromatic hydrocarbons using shape-selective catalyst materials is well-known. U.S. Pat. No. 3,756,942 to Cattanach teaches such a method using a zinc-exchanged ZSM-5. U.S. Pat. No. 4,180,689 to Davies et al teaches conversion of $C_3$-$C_{12}$ hydrocarbons to aromatics using a gallium-activated zeolite such as ZSM-5, ZSM-11, ZSM-12 or ZSM-35 which is gallium-exchanged or gallium impregnated. Although the incorporation of a metal of mild dehydrogenation function such as zinc or gallium activates the catalyst for aromatization reactions, loss of the metal, for example by elution, commonly occurs under the high temperature reducing conditions encountered in aromatization. U.S. Pat. No. 4,490,569 to Chu et al teaches a method to reduce such elution by incorporating gallium as well as zinc into a zeolite aromatization catalyst. All of these U.S. patents are incorporated herein by reference.

SUMMARY OF THE INVENTION

There is provided a process for producing aromatic hydrocarbons which comprises contacting a feed containing non-aromatic $C_2$-$C_{12}$ hydrocarbons with a catalyst at a pressure of about atmospheric to 1000 psig, a weight hourly space velocity of about 0.05 to 300 and a temperature of about 204° to 675° C., wherein said catalyst comprises a layered silicate and pillars of an oxide of at least one element selected from Groups IB, IIB, IIIA, IIIB, IVA, IVB, VA, VB, VIA, VIIA and VIIIA of the Periodic Table of the Elements separating the layers of the silicate, said catalyst comprising at least one element selected from gallium and zinc.

EMBODIMENTS

Many layered materials are known which have three-demensional structures which exhibit their strongest chemical bonding in only two dimensions. In such materials, the stronger chemical bonds are formed in two-dimensional planes and a three-dimensional solid is formed by stacking such planes on top of each other. However, the interactions between the planes are weaker than the chemical bonds holding an individual plane together. The weaker bonds generally arise from interlayer attractions such as Van der Waals forces, electrostatic interactions, and hydrogen bonding. In those situations where the layered structure has electronically neutral sheets interacting with each other solely through Van de Waals forces, a high degree of lubricity is manifested as the planes slide across each other without encountering the energy barriers that arise with strong interlayer bonding. Graphite is an example of such a material. The silicate layers of a number of clay materials are held together by electrostatic attraction mediated by ions located between the layers. In addition, hydrogen bonding interactions can occur directly between complementary sites on adjacent layers, or can be mediated by interlamellar bridging molecules.

Laminated materials such as clays may be modified to increase their surface area. In particular, the distance between the interlamellar layers can be increased substantially by absorption of various swelling agents such as water, ethylene glycol, amines, ketones, etc., which enter the interlamellar space and push the layers apart. However, the interlamellar spaces of such layered materials tend to collapse when the molecules occupying the space are removed by, for example, exposing the clays to high temperatures. Accordingly, such layered materials having enhanced surface area are not suited for use in chemical processes involving even moderately severe conditions.

The extent of interlayer separation can be estimated by using standard techniques such as X-ray diffraction to determine the basal spacing, also known as "repeat distance" or "d-spacing". These values indicate the distance between, for example, the uppermost margin of one layer with the uppermost margin of its adjoining layer. If the layer thickness is known, the interlayer spacing can be determined by subtracting the layer thickness from the basal spacing.

The aromatization catalyst employed in the present invention comprises a layered silicate containing interspathic polymeric oxide such as silica. The interlayer distance of the silicate may be such that polycyclic hydrocarbons can pass between adjacent layers of the silicate, preferably a distance greater than about 10 angstroms or even 15 angstroms, say about 15 to 20 angstroms. Aromatization activity can be enhanced by incorporating gallium, zinc or both into the catalyst.

The process of the present invention utilizes an aromatization catalyst which comprises a layered silicate which contains interspathic polymeric silica. The layered silicate may also comprise an interspathic polymeric oxide of an element selected from the group consisting of Al, B, Cr, Ga, In, Mo, Nb, Ni, Ti, Tl, W and Zr, e.g., polymeric silica-alumina between the layers of the silicate material. Preferably, such "pillared" materials are thermally stable, i.e., capable of withstanding calcining at a temperature of about 450° C. for at least 2 hours without significant reduction (e.g., not greater than 10 to 20%) in the spacing between the silicate layers. Preferably, such materials can withstand prolonged exposure to the conditions encountered during aromatization. Polymeric interspathic silicas displaced between silicate layers are considered to include oxides of two or more repeating units, preferably three or more repeating units, e.g., four or more or even five or more repeating units. The extent of polymerization of the interspathic polymeric silica is believed to affect the ultimate interlayer separation of the layered product; that is to say, the greater the extent of polymerization occurring, the greater the interlayer distance resulting in the pillared layered silicate. A layered material suited for use in the present aromatization process, having a desired interlayer spacing can be prepared according to the method set out in U.S. Pat. No. 4,859,648, incorporated herein by reference. In this method, the interlayer spacing of the layered material can be tailored by careful selection of the "propping" agent used to separate the layers during treatment with interspathic polymeric silica precursors which are eventually converted to the thermally stable polymeric silica "pillars." Indeed, a wide range of interlayer spacings can be achieved by this method. Interlayer distances can range anywhere from 2 to 30 angstroms or more, e.g., greater than 5, 10, 15 or 20 angstroms, depending largely on the type of "propping" agent used as well as the layered silicate being treated.

The pillared layered silicates employed herein can be prepared by treating a layered silicate which contains ion exchange sites having interspathic cations associated therewith, with an organic compound which is a cationic species or capable of forming a cationic species to effect exchange with the interspathic cations. An electrically neutral compound capable of conversion to the interspathic polymeric metal or non-metal oxide is provided between layers of the treated layered silicate. The compound is then converted to the interspathic polymeric silica to form the layered material.

The pillared layered silicate employed in the present invention can be prepared by treating a layered silicate, e.g., a high silica alkali silicate such as synthetic magadiite, or synthetic kenyaite. These pillared layered silicate materials possess a framework composed essentially of only tetrahedral sheets, i.e., silicon is coordinated with four oxygen atoms, condensed on each other. These materials lack octahedral sheets, such as those found in clays, wherein an element such as aluminum is coordinated with six oxygen atoms. Besides interspathic polymeric silica, interspathic polymeric oxides of one or more elements selected from the group consisting of B, Al, Ga, In and Tl can also be incorporated between the layers of the silicate either separate from or incorporated into the interspathic polymeric silica pillars. Interspathic polymeric alumina is particularly useful in imparting acidic activity to the layered silicate. Interspathic polymeric oxides containing silica-alumina are a preferred pillar for these layered silicates.

Pillared silicates containing from 5 to 50 wt% silica-alumina incorporated as the pillar material are desirable. Particularly preferred are silicates containing from about 10 to 20 wt% silica-alumina as the pillared material. The silica/alumina molar ration ($SiO_2/Al_2O_3$) of the pillared material may vary between about 5 to 1000 or even greater.

Layered silicate materials of relatively high interplanar distance (d-spacing), e.g., greater than about 10, 15, 18, 20, 25, or even 30 or more angstroms, can be prepared using the above-discussed techniques. These materials are capable of being exposed to severe conditions such as those encountered in calcining, e.g., at temperatures of about 450° C. for about two or more hours, e.g., four hours, in nitrogen or air, without significant decrease, say, e.g., less than about 10%, in interlayer distance. The size of interspathic polymeric silica contained within the final product can be greatly varied because the polymeric silica precursor species are introduced in an electrically neutral form such that the amount of interspathic material incorporated within the layered silicate is not dependent upon the charge density of the original layered silicate starting material. Charge density should be taken into consideration in determining the suitability of the cationic species introduced between the layers in the procedure used to prop open the layers prior to pillaring. The use of an electrically neutral polymeric oxide precursor allows the formation of materials in which the interlayer spacing can be widely varied.

The layered silicate starting material can contain ion exchange sites having interspathic cations associated therewith. Such interspathic cations may include hydrogen ion, hydronium ion or alkali metal cation. The starting material is treated with a "propping" agent comprising a source of organic cation, which source may include the cation itself, in order to effect an exchange of the interspathic cations resulting the layers of the starting material being propped apart. In particular, alkylammonium cations have been found useful. Thus $C_3$ and larger alkylammonium cations, e.g., n-octylammonium, can be readily incorporated within the interlayer species of the layered silicates, serving to prop open the layers in such a way as to allow incorporation of the polymeric oxide precursor. The extent of the interlayer spacing can be controlled by the size of the organoammonium ion employed so that use of the n-propylammonium cation can achieve a d-spacing of about 2 to 5A or an opening of about 2-3A, whereas to achieve a d-spacing opening of 10 to 20A, an n-octylammonium cation or a cation of equivalent length is required. The organic ammonium cations separating the silicate layers may also be formed in situ by reaction of the neutral amine species with interlayer hydrogen or hydronium cations of the layered silicate starting material.

The polymeric oxide pillars are formed from a precursor material which is preferably introduced between the layers of the organic "propped" species as a cationic, or more preferably, electrically neutral, hydrolyzable compound of the desired elements. The precursor material is preferably an organic compound containing said desired elements which is a liquid under ambient conditions. In particular, hydrolyzable compounds, e.g., alkoxides, of the desired elements of the pillars are utilized as the precursors. Suitable polymeric silica precursor materials include tetraalkylsilicates, e.g., tetrapropylorthosilicate, tetramethylorthosilicate and, most preferably, tetraethylorthosilicate. Introduction of interspathic polymeric oxide of an element selected from the group consisting of Al, B, Cr, Ga, In, Mo, Nb, Ni, Ti, Tl, W, and Zr to the pillar system can be achieved by contacting a hydrolyzable compound of the desired element with the organic "propped" species before, after or simultaneously with the contacting of the layered chalcogenide with the silicon compound. The hydrolyzable aluminum compound employed may be an aluminum alkoxide, e.g., aluminum isopropoxide.

After hydrolysis to produce the polymeric oxide pillars and calcination to remove the organic propping agent, the final pillared product may contain residual exchangeable cations. Such residual cations in the layered material can be ion exchanged by known methods with other cationic species to provide or alter the catalytic activity of the pillared product. In particular, gallium or zinc components can be introduced by ion-exchange or impregnation techniques known in the art. Representative ion exchange techniques are disclosed in a wide variety of patents including U.S. Pat. Nos. 3,140,249; 3,140,251; and 3,140,253, all of which are incorporated herein by reference. Generally, the aromatization catalyst of the present invention can contain about 0.1 to 20 weight percent, preferably about 0.5 to 15 weight percent of gallium or zinc.

The polymeric oxide precursor-containing product can be exposed to suitable conversion conditions, such as hydrolysis and/or calcination to form the layered material employed in the present invention. The hydrolysis step may be carried out by any method. Because of the effect of interspathic water on hydrolysis, the extent of hydrolysis may be modified by varying the extent to which the organic-"propped" species is dried prior to addition of the polymeric oxide presursor. As noted earlier, the product after conversion to the polymeric oxide form may be exposed to conditions which remove organic compounds such as the organic cation propping agents, e.g., exposure to elevated temperatures such as those encountered by calcining in air or nitrogen. Such products, especially when calcined, exhibit high surface area, e.g., greater than 200, 300, 400 or even 600 m$^2$/g, and thermal and hydrothermal stability.

The pillared silicates can be composited with porous inorganic oxide matrix materials such as silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of pillared silicate component and inorganic matrix, on an anhydrous basis, may vary widely with the silicate content ranging from about 1 to about 99 percent by weight and more usually in the range of from about 5 to about 80 percent by weight of the dry composite.

Layered silicates, e.g., high silica alkali silicates such as magadiite, natrosilite, kenyaite, makatite, nekoite, kanemite, okenite, dehayelite, macdonaldite and rhodesite, unlike swellable clays, lack octahedral sheets, i.e., sheets composed of atoms which are octahedrally coordinated with oxygen atoms. Such high silica alkali silicates, as well as their synthetic analogues are well-suited as starting materials used in preparing the pillared layered silicates employed in the process of the present invention. Without stable intercalated pillars, these starting materials tend to undergo collapse of their layers at elevated temperatures, which results in low porosity and low surface area.

The layered silicate starting materials known as high silica alkali silicates, whose layers lack octahedral sheets, can be prepared hydrothermally from an aqueous reaction mixture containing silica and caustic at relatively moderate temperatures and pressures. These layered silicates may contain tetracoordinate framework atoms other than Si. Such layered silicates can be prepared by co-crystallizing in the presence of non-silicon tetravalent elements, e.g., those selected from the group consisting of B, Al, Ga, In and Tl as well as any other such elements which are catalytically useful when incorporated in the silicate structure. Alternatively, non-silicon framework elements already in a layered silicate may be substituted by a tetracoordinate element. Both co-crystallized and substituted layered high silica alkali silicates may be treated by the procedure described above to provide layered materials containing interspathic polymeric oxide pillars.

Synthetic magadiite materials which contain interspathic polymeric oxides may be particularly suited to use in the aromatization process of the present invention. Synthetic magadiite is readily synthesized hydrothermally from a reaction mixture containing inexpensive sources of silica and caustic. Tetracoordinate elements other than silicon, e.g., those selected from the group consisting of B, Al, Ga, In, Tl and other catalytically useful metals, may be added to the reaction mixture to produce synthetic magadiite layered silicates. Preferably, such elements are selected from the group consisting of Al and Ga. An organic directing agent may also be added to the reaction mixture. The reaction mixture for synthetic layered silicate materials can be described in molar ratios as follows:

| | |
|---|---|
| $SiO_2/X_2O_3 =$ | 10 to infinity where X can be B, Al, B, Ga, In and/or Tl or other catalytically useful metal |
| $M^+OH^-/SiO_2 =$ | 0 to 0.6, (preferably 0.1–0.6) M = an alkali metal |
| $H_2O/SiO_2 =$ | 8–500 |
| $R/SiO_2 =$ | 0–0.4 | where R can be an organic such as benzyltriethylammonium chloride, benzyltrimethylammonium chloride, dibenzyldimethylammonium chloride, N,N'-dimethylpiperazine, triethylamine, or other quaternary compounds or heterocyclic amines.

The reaction mixture can be maintained at a temperature of about 100° to 200° C. for anywhere from about 1 to 150 days in order to form a product having the following composition:

| | |
|---|---|
| % N = | 0 to 3, e.g., 0 to 0.3 |
| $SiO_2/X_2O_3 =$ | 10 to infinity where X may be in tetrahedral or octahedral position |
| $M_2O/SiO_2 =$ | 0 to 0.5, e.g., 0.05–0.1 |

The synthetic layered silicate materials thus prepared have a low surface area. Introduction of interspathic polymeric oxides according to the above-described procedure can increase the surface area of these materials. Generally, the synthetic magadiite (or layered silicate) material is acidified by any suitable means, e.g., treatment with aqueous 0.1 N HCl, and thereafter treated with a "propping" agent. A suitable compound capable of conversion to a polymeric oxide is combined with the "propped" layered silicate and the resulting material can then be calcined to remove residual organics.

Another embodiment of the present invention involves aromatization reactions using synthetic kenyaite materials which contain interspathic polymeric oxides. Kenyaite, a layered silica acid which is known to exist in nature as a sodium salt Na can be prepared in the potassium form $K_2Si_{22}O_{45}$·10 $H_2O$ in the laboratory. Synthetic kenyaite is readily synthesized hydrothermally from a reaction mixture containing inexpensive sources of silica and caustic, preferably KOH. Tetracoordinate elements other than silicon, e.g., those selected from the group consisting of Al, B, Cr, Fe, Ga, In, Ni, Zr and other catalytically useful metals, may be added to the reaction mixture to produce synthetic kenyaite layered silicates. $Al(NO_3)_3$·9$H_2O$ and aluminum-tri-sec-butoxide are suitable reagents for the introduction of non-silicon tetracoordinate elements in the kenyaite framework. Co-crystallizing with B, Al, and/or Zr is particularly preferred. The reaction mixture may also be seeded with kenyaite.

The present aromatization reaction involves contacting a suitable feedstock with the present catalyst under sufficient aromatization conditions. Such conditions may include a pressure of about atmospheric to 1000 psig, preferably about atmospheric to 200 psig; a weight hourly space velocity of about 0.05 to 300, preferably about 0.2 to 10; and a temperature of about 204° to 675° C., preferably about 315° to 593° C.

The feedstock may include one or more $C_2$ to $C_{12}$ non-aromatic hydrocarbons, especially, $C_6$ to $C_{12}$ paraffins, most especially, n-paraffins.

EXAMPLE 1

Silica/gallium pillared kenyaite was prepared by suspending 80 grams of a silica-kenyaite which had been swollen directly with cetyldimethylethylammonium bromide and impregnated with tetraethylorthesilicate (TEOS) in 200 g of 0.5M $Ga(NO_3)_3$. The slurry was stirred for 2 hours then filtered, air dried, and calcined for 3 hours at 540° C.

The finished material had the following properties:

| | |
|---|---|
| Surface Area, $m^2/g$ | 593 |
| Ash, 1000° C., wt % | 93.3 |
| $SiO_2$, wt % | 87.2 |
| Ga, wt % | 4.2 |
| $Al_2O_3$, ppm | 720 |

EXAMPLE 2

Silica/alumina-pillared silica-kenyaite was prepared in an analogous manner to that described in Example 1 where 200g of the silicate was suspended in 1000g of 0.5N $Al(NO_3)_3$. The slurry was stirred for 18 hours, filtered, air dried, and then calcined in air for 6 hours at 540° C.

The finished material had the following properties:

| | |
|---|---|
| Surface Area, $m^2/g$ | 582 |
| Ash, 1000° C., wt % | 90.58 |
| $SiO_2$, wt % | 85.3 |
| $Al_2O_3$, wt % | 2.9 |
| K, ppm | 305 |

EXAMPLE 3

A sample of ZSM-5 was prepared according to the procedure of Argauer and Landolt as set forth in U.S. Pat. No. 3,702,886. This sample was then carefully calcined in flowing (10 v/v/min) nitrogen at a heating rate of 0.5° C./min to 538° C., held at the final temperature for three hours after which the atmosphere was changed to flowing (10 v/v/min) dry air. After the ZSM-5 catalyst was cooled to room temperature, it was ion exchanged twice at RT using 5 cc/g of a 1.0N $NH_4NO_3$ solution. The catalyst was rinsed thoroughly with deionized water between exchanges. After drying the ZSM5 catalyst overnight at 120° C., the catalyst was calcined in flowing (10 v/v/min) dry air at 0.1° C./min to 538° C. and held at this temperature in flowing air for three hours.

The final catalyst had the following properties:

| | |
|---|---|
| $SiO_2$, wt % | 94.2 |
| $Al_2O_3$, wt % | 2.03 |
| Na, ppm | 350 |
| Ash at 1000° C., wt % | 96.5 |

EXAMPLE 4

The three catalysts from Examples 1, 2, 3 were pelleted, crushed, and sized to 40/80 mesh and then loaded into 0.64 cm ID tubular quartz reactors. These catalysts were then preheated to 538° C. in flowing helium (200 cc/min) at a heating rate of 30° CC/min. After the catalysts reached reaction temperature (538° C.), the helium stream from each reactor was diverted through a liquid sparger unit which was filled with n-hexane (98.9% n-hexane percolated through $Al_2O_3$). The helium-hexane mixture was cooled to 15.9° C. using a circulating glycol cooled condenser to guarantee that the hexane partial pressure was 100 torr (13.3 kPa).

The helium flow rate was adjusted to obtain an n-hexane conversion ranging from 5 to 25 wt%. Over the course of one hour, six analyses were performed on each catalyst to determine activity and relative aging rates. The results of the analyses of each of these three catalysts are given in Tables 1, 2, and 3. Here, benzene selectivity is defined as follows: Benzene Selectivity $$\frac{100 \times wt\ \%\ \text{Benzene in product}}{wt\ \%\ \text{non n-}C_6\ \text{components in product}}$$

and k is the reaction rate constant in $sec^{-1}$, assuming first order kinetics for the conversion of n-hexane.

TABLE 1

N-Hexane Conversion over Pillared Layered Gallosilicate Catalyst of Example 1

| Time-on Stream | Temp. (°C.) | Flow Rate (cc/min) | % Conv on n-$C_6$ | Benzene Select. | k, $sec^{-1}$ × $10^4$ |
|---|---|---|---|---|---|
| 12 min | 538.5 | 22.8 | 9.9 | 30.1 | 2.07 |
| 24 min | 538.2 | 22.8 | 12.0 | 37.2 | 2.57 |
| 35 min | 538.2 | 22.8 | 11.6 | 39.5 | 2.48 |
| 47 min | 538.2 | 22.8 | 10.6 | 40.7 | 2.25 |
| 58 min | 538.2 | 22.7 | 9.9 | 41.1 | 1.94 |
| 70 min | 538.0 | 22.8 | 9.2 | 41.5 | 1.94 | notes:
Flow Rate of Helium is measured at 25° C. and 1 atm.

TABLE 2

N-Hexane Conversion over Pillared Layered Gallium-Free Silicate Catalyst of Example 2
Total Amount of Catalyst Loaded = 0.243 grams

| Time-on Stream | Temp. (°C.) | Flow Rate (cc/min) | % Conv on n-$C_6$ | Benzene Select. | k, $sec^{-1}$ × $10^4$ |
|---|---|---|---|---|---|
| 12 min | 538.9 | 22.7 | 7.5 | 1.1 | 1.30 |
| 24 min | 539.2 | 22.7 | 6.0 | 0.7 | 1.02 |
| 36 min | 539.4 | 22.7 | 6.1 | 0.5 | 1.05 |
| 47 min | 539.2 | 22.7 | 6.4 | 0.7 | 1.08 |
| 59 min | 539.2 | 22.7 | 6.3 | 0.5 | 1.08 |
| 68 min | 539.2 | 22.7 | 6.4 | 0.5 | 1.11 | notes:
Flow Rate of Helium is measured at 25° C. and 1 atm.

TABLE 3

N-Hexane Conversion over ZSM-5 Catalyst of Example 3
Total Amount of Catalyst Loaded = 0.106 grams

| Time-on Stream | Temp. (°C.) | Flow Rate (cc/min) | % Conv on n-$C_6$ | Benzene Select. | k, $sec^{-1}$ × $10^4$ |
|---|---|---|---|---|---|
| 11 min | 536.5 | 94.2 | 20.4 | 0.3 | 39.7 |
| 21 min | 536.2 | 93.9 | 20.4 | 0.5 | 39.7 |
| 30 min | 536.2 | 93.5 | 20.3 | 0.5 | 39.2 |
| 39 min | 536.2 | 93.2 | 20.5 | 0.5 | 39.5 |
| 49 min | 536.2 | 92.8 | 20.3 | 0.5 | 38.9 |
| 59 min | 536.0 | 92.5 | 20.3 | 0.5 | 38.7 | notes:
Flow Rate of Helium is measured at 25° C. and 1 atm.

A comparison of these results shows that the benzene selectivity is the highest over the pillared gallosilicate. Note that after nearly one hour on stream the benzene selectivity of this material is still increasing. Thus, the maximum benzene selectivity for the pillared gallosilicate will be in excess of 41% compared to 0.5 to 1.0% over the pillared gallium-free layered silicate of Example 2 and approximately 0.5% for the ZSM-5 catalyst.

Table 1 and 2 also show that the gallosilicate is more active and at least as stable as the analogous gallium-free material. After an hour on stream, the rate constant of the gallosilicate has declined less than 8% (from $2.07 \times 10^{-4} \sec^{-1}$ to $1.94 \times 10^{-4} \sec^{-1}$) compared to an approximate 15% decline in activity (x drops from $1.30 \times 10^{-4} \sec^{-1}$ to $1.11 \times 10^{-4} \sec^{-1}$) for the pillared gallium-free layered silicate. This high degree of stability of the pillared layered gallosilicate is unexpected in view of its high aromatic selectivity. Generally, under equivalent reaction conditions high aromatic selectivity corresponds to faster catalyst aging rates since aromatics, and particularly alkyl aromatics, tend to condense and form coke on the catalysts, C. H. Bartholomew, "Catalyst Deactivation", Chem. Engineering, 91, Nov. 12, 1984, p. 96. This coke in turn restricts the pores of the catalyst and covers the active sites thereby damaging conversion activity.

EXAMPLE 5

Tables 4 and 5 compare the product distributions from the conversion of n-hexane over the pillared layered gallosilicate and gallium-free silicate, respectively. These data show that the gallosilicate also consistently produces higher levels of highly desirable toluene and lower levels of less desirable $C_3$'s. The light gas selectivities ($C_1+C_2$, $C_3^-$, and $C_4^-$) all decline while the toluene and benzene selectivities increase with time on stream. Again, this result is unexpected since ZSM-5 based catalysts for this type of reaction show a consistent loss in activity with time on stream.

TABLE 4

Product Distribution from N-Hexane Conversion over Pillared Layered Gallosilicate of Example 1

| Time-on-Stream, min | 12 | 24 | 35 | 47 | 58 | 70 |
|---|---|---|---|---|---|---|
| Temperature, °C. | 538.5 | 538.2 | 538.2 | 538.2 | 538.2 | 538.0 |
| GHSV, hr$^{-1}$ | 3734 | 3745 | 3742 | 3738 | 3734 | 3731 |
| % N-Hexane Conversion, wt % | 9.9 | 12.0 | 11.6 | 10.6 | 9.9 | 9.2 |
| Product Distribution, wt % | | | | | | |
| $C_1 + C_2$ | 1.56 | 1.69 | 1.47 | 1.29 | 1.17 | 1.07 |
| $C_3$'s | 1.95 | 2.07 | 1.78 | 1.58 | 1.43 | 1.32 |
| i-$C_4$ | 2.13 | 2.24 | 1.95 | 1.17 | 1.55 | 1.42 |
| n-$C_4$ | 0.36 | 0.41 | 0.01 | 0.01 | 0.01 | 0.01 |
| $C_4^=$'s | 0.01 | 0.01 | 0.01 | 0.01 | 0.01 | 0.01 |
| i-$C_5$ | 0.02 | 0.02 | 0.02 | 0.01 | 0.01 | 0.01 |
| n-$C_5$ | 0.03 | 0.03 | 0.03 | 0.03 | 0.03 | 0.03 |
| i-$C_6$ | 0.10 | 0.07 | 0.08 | 0.07 | 0.07 | 0.07 |
| n-$C_6^=$ | 88.96 | 86.86 | 87.30 | 88.25 | 88.98 | 89.70 |
| $C_6$'s | 0.41 | 0.40 | 0.45 | 0.46 | 0.48 | 0.50 |
| Benzene | 3.02 | 4.51 | 4.62 | 4.38 | 4.12 | 3.86 |
| Toluene | 0.15 | 0.31 | 0.40 | 0.42 | 0.40 | 0.37 |
| Other $C_7+$ | 1.09 | 1.10 | 1.05 | 1.15 | 1.17 | 0.17 |
| Unknowns | 0.24 | 0.29 | 0.33 | 0.32 | 0.31 | 0.26 |
| Benzene Selectivity, wt % | 30.1 | 37.2 | 39.5 | 40.7 | 41.1 | 41.5 |
| Toluene Selectivity, wt % | 1.5 | 2.6 | 3.4 | 4.0 | 4.0 | 4.0 |
| $C_2^-$ Selectivity, wt % | 15.8 | 14.1 | 12.7 | 12.2 | 11.8 | 11.6 |
| $C_3^-$ Selectivity, wt % | 35.5 | 31.3 | 28.0 | 27.1 | 26.3 | 25.0 |
| $C_4$ Selectivity, wt % | 60.7 | 53.5 | 48.0 | 46.2 | 44.8 | 44.2 |

TABLE 5

Product Distribution from N-Hexane Conversion over Silica-Alumina Pillared Layered Silicate of Example 2

| Time-on-Stream, min | 12 | 24 | 36 | 47 | 59 | 68 |
|---|---|---|---|---|---|---|
| Temperature, °C. | 538.9 | 539.2 | 539.4 | 539.2 | 539.2 | 539.2 |
| GHSV, hr$^{-1}$ | 3069 | 3064 | 3064 | 3065 | 3065 | 3065 |
| % N-Hexane Conversion, wt % | 7.5 | 6.0 | 6.1 | 6.4 | 6.3 | 6.4 |
| Product Distribution, wt % | | | | | | |
| $C_1 + C_2$ | 1.03 | 0.88 | 0.89 | 0.89 | 0.91 | 0.92 |
| $C_3$'s | 4.73 | 3.79 | 3.85 | 3.93 | 3.98 | 4.04 |
| i-$C_4$ | 1.07 | 0.89 | 0.90 | 0.91 | 0.91 | 0.93 |
| n-$C_4^=$ | 0.18 | 0.15 | 0.15 | 0.15 | 0.16 | 0.15 |
| $C_4^=$'s | 0.01 | 0.01 | 0.01 | 0.01 | 0.01 | 0.01 |
| i-$C_5$ | 0.20 | 0.17 | 0.18 | 0.18 | 0.19 | 0.19 |
| n-$C_5$ | 0.06 | 0.05 | 0.05 | 0.05 | 0.05 | 0.05 |
| i-$C_6$ | 0.31 | 0.22 | 0.25 | 0.29 | 0.30 | 0.32 |
| n-$C_6^=$ | 91.30 | 92.90 | 92.80 | 92.51 | 92.54 | 92.45 |
| $C_6$'s | 0.58 | 0.58 | 0.59 | 0.61 | 0.60 | 0.61 |
| Benzene | 0.08 | 0.04 | 0.03 | 0.04 | 0.03 | 0.03 |
| Toluene | 0.02 | 0.02 | 0.01 | 0.01 | 0.01 | 0.01 |
| Other $C_7+$ | 0.25 | 0.33 | 0.17 | 0.28 | 0.17 | 0.18 |
| Unknowns | 0.40 | 0.13 | 0.29 | 0.13 | 0.13 | 0.13 |
| Benzene Selectivity, wt % | 1.07 | 0.69 | 0.50 | 0.65 | 0.45 | 0.46 |
| Toluene Selectivity, wt % | 0.2 | 0.3 | 0.2 | 0.1 | 0.1 | 0.1 |
| $C_2^-$ Selectivity, wt % | 13.7 | 14.7 | 14.6 | 13.9 | 14.4 | 14.4 |
| $C_3^-$ Selectivity, wt % | 76.8 | 77.8 | 77.7 | 75.3 | 77.6 | 77.5 |

TABLE 5-continued

Product Distribution from N-Hexane Conversion over Silica-Alumina Pillared Layered Silicate of Example 2

| C$_4$ Selectivity, wt % | 93.6 | 95.3 | 95.1 | 92.0 | 94.8 | 94.5 |

IT IS CLAIMED:

1. A process for producing aromatic hydrocarbons which comprises contacting a feed containing non-aromatic C$_2$ to C$_{12}$ hydrocarbons with a catalyst at a pressure of about atmospheric to 1000 psig, a weight hourly space velocity of about 0.05 to 300 and a temperature of about 204° to 675° C., wherein said catalyst comprises a layered silicate and pillars of an oxide of at least one element selected from Groups IB, IIB, IIIA, IIIB, IVA, IVB, VA, VB, VIA, VIIA and VIIIA of the Periodic Table of the Elements separating the layers of the silicate, said catalyst comprising at least one element selected from gallium and zinc.

2. The process of claim 1, wherein said pressure ranges from about atmospheric to 200 psig, said weight hourly space velocity ranges from about 0.2 to 20 and said temperature ranges from about 315° to 593° C.

3. The process of claim 1, wherein the pillars comprise polymeric silica.

4. The process of claim 3, wherein said layered silicate is magadiite.

5. The process of claim 3, wherein said layered silicate is kenyaite.

6. The process of claim 1, wherein said pillars comprise silica-alumina.

7. The process of claim 5, wherein said catalyst contains gallium.

8. The process of claim 6, wherein said feed is n-hexane.

9. The process of claim 1, wherein said catalyst contains zinc.

* * * * *